US00PP14110P39

(12) United States Plant Patent
Zerr

(10) Patent No.: US PP14,110 P3
(45) Date of Patent: Aug. 26, 2003

(54) POINSETTIA PLANT NAMED 'FISMOND'

(75) Inventor: Katharina Zerr, Hohr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/108,422

(22) Filed: Mar. 29, 2002

(65) Prior Publication Data

US 2002/0157156 P1 Oct. 24, 2002

(30) Foreign Application Priority Data

Apr. 23, 2001 (EP) ..... 2001/0723

(51) Int. Cl.[7] ..... A01H 5/00
(52) U.S. Cl. ..... Plt./307
(58) Field of Search ..... Plt./307, 303

*Primary Examiner*—Bruce R. Campell
*Assistant Examiner*—June Hwu
(74) *Attorney, Agent, or Firm*—Foley & Lardner

(57) ABSTRACT

A new and distinct Poinsettia plant named 'Fismond' characterized by having deep red bract color; bracts with smooth surface, weak lobes, tightly arranged; dark green foliage with weak lobes; moderately compact and round plant habit; begin of flowering late with good keeping quality; suitable especially for late sale short before or during the holiday season.

1 Drawing Sheet

Latin name of the genus and species of the plant claimed: *Euphorbia pulcherrima.*
Variety denomination: 'Fismond'.

BACKGROUND OF THE INVENTION

The present invention relates to a new and distinct cultivar of Poinsettia plant known by the cultivar name 'Fismond', and botanically known as *Euphorbia pulcherrima*. 'Fismond' is a product of a planned breeding program which had the objective of creating new Poinsettia cultivars with red flower color in combination with dark-green foliage and good cultivation ability. 'Fismond' originated from a hybridization made by Katharina Zerr, the inventor, in Hillscheid, Germany, in 1996.

The female parent was a proprietary hybrid seedling, number S 1202–1, which was characterized by red bract color, medium green foliage, and compact growth. The male parent was the variety 'Fiscor' (U.S. Plant Pat. No. 9,364), having deep red bract color, dark green foliage, and relatively wide plant habit.

The seeds germinated in the spring of 1997, and the resulting seedlings were identified by numbers. In the summer of 1997, a cutting was taken from each seedling, rooted and grown out for examination as flowering single-stem plants. 'Fismond' was discovered and selected as one flowering plant (no. 7136) within the progeny of the stated cross by Katharina Zerr in December 1997. After this plant had been chosen, more cuttings were taken from the original seedling and grafted on rootstocks of the variety 'Beckmann's Altrosa' (U.S. Plant Pat. No. 9,336), in order to transmit the branching causing agent, phytoplasma, into the clone to improve the branching characteristics. From the upper area of the successfully grafted plants, shoot tip cuttings were taken for the cultivation of branched plants for the second examination in the fall of 1999.

Horticultural examination of the clone starting in 1999 and continuing thereafter has confirmed that the combination of characteristics as herein disclosed for 'Fismond' are firmly fixed and retained through successive generations of asexual reproduction.

SUMMARY OF THE INVENTION

The following traits have been repeatedly observed and are determined to be basic characteristics of 'Fismond' which in combination distinguish this Poinsettia as a new and distinct cultivar:

1. deep red bract color;
2. bracts with smooth surface, weak lobes, tightly arranged;
3. dark green foliage with weak lobes;
4. moderately compact and round plant habit;
5. begin of flowering late with good keeping quality;
6. suitable especially for late sale short before or during the holiday season.

'Fismond' has not been observed under all possible environmental conditions. The phenotype may vary significantly with variations in environment such as temperature, light intensity, and day-length. The following observations, measurements and comparisons describe plants grown in Hillscheid, Germany, under greenhouse conditions which approximate those generally used in commercial practice.

Of the many commercial cultivars known to the inventor, the most similar in comparison to 'Fismond' is the parent cultivar 'Fiscor'. In comparison to 'Fiscor', 'Fismond' has somewhat smaller bracts, it develops more slowly and is therefore suitable for late sales, without having to delay initiation of flowers by applying additional light (long day conditions) from mid September to early October.

BRIEF DESCRIPTION OF THE DRAWING

The accompanying color photographic drawing shows typical inflorescence and foliage of 'Fismond', with colors being as true as possible with an illustration of this type. The photograph shows a mature potted plant.

DETAILED BOTANICAL DESCRIPTION

The plants described were grown in a greenhouse in Langley, British Columbia, Canada, in the fall of 2001. Rooted cuttings were planted into 6 inch pots on July 18, and were pinched on August 13, leaving 7 leaves. Initially, the minimum temperature was between 22° C. (minimum) and 24.5 C. (maximum, ventilation temperature), from September to late October between 18° and 21° C., and 15° to 17° C. in November. The plants initiated flowers under short-day conditions after applying shading (black-out) from September 10. Observations and measurements were mainly taken around November 18, when the plants were 17.5 weeks old and when most varieties had begun flowering, while 'Fismond' was still somewhat immature.

In the following description color references are made to The Royal Horticultural Society Colour Chart (R.H.S.). The color values were determined indoors in a north light.

Classification:
Botanical: *Euphorbia pulcherrima.*
Commercial: Poinsettia, cv. Fismond.
Parentage:
*Seedling.*—Female parent: S 1202-1, proprietary plant. Male parent: cultivar 'Fiscor' (U.S. Plant Pat. No. 9,364).
Plant:
*Form.*—Shrub, self-branching.
*Growth habit.*—Relatively compact, weak to medium vigor, pinched plants are bushy and round in shape.
*Height.*—29 cm (in 6 inch pot, above soil line).
*Width.*—56 cm.
*Average number of branches.*—7.
*Average number of inflorescence.*—6.8.
*Stem color.*—Lower part: green, RHS 147 C, partly reddish infused, RHS 182 A to 182 B.
*Rooting.*—Medium, sufficiently rooted for transplanting after about 20–24 days in a greenhouse at a temperature of 22–24° C.
*Blooming habit.*—Begin under natural short day conditions in fall: botanically (cyathia open): in mid December; commercially (bracts colored, marketable): in mid December.
*Flowering response time.*—About 11 weeks.
*Flowering season.*—Mainly from mid December to early January.
*Keeping quality.*—Good quality will be maintained for about 6 weeks.
Foliage:
*Shape.*—Ovate, with rounded base, weak, rounded lobes and acuminate tip.
*Margin.*—Entire, apart from the lobes.
*Texture.*—Upper surface: Smooth and flat, only weakly veined, color of the veins: light green, RHS 143 D, and red, RHS 46 C, at the base of the midrib. Lower surface: Flat and smooth, except for the slightly protruding midrib and finer side veins in a pinnate pattern, the color of the midrib is pink, RHS 48 B.
*Size.*—Leaf blade: Length: 12.35 cm. Width: 8.75 cm. Petiole: Length: 6.75 cm.
*Quantity.*—About 50 leaves per plant.
*Color.*—Generally dark green, uniform. Mature foliage: upper surface, near RHS 139 A under surface, RHS 138 A. New foliage: upper surface: RHS 143 A under surface: RHS 137 D.
*Leaf petiole.*—Upper side: dark purple, RHS 60 A lower side: dull purple, RHS 60 B.
*Aspect.*—Petioles are horizontally directed, while the leaf blades showing slightly downward.
Disease resistance: No special observations made.
Flowering description: Whole inflorescence with surrounding bracts: just under medium-sized, star-shaped, flat, with the bracts horizontally directed in a tight arrangement, and overlapping.
*Diameter.*—Approximately 25–26 cm.
*Number of bracts per inflorescence.*—11–13 (size over 2 cm).
*Keeping quality.*—Keeps well throughout January even under unfavorable conditions, no fading of bract color, no dropping of bracts, little or no dropping of leaves.
Bracts:
*Shape.*—Ovate, with rounded bases, very weak to weak lobes, and acuminated tips.
*Size.*—13.25 cm long, 9.5 cm wide.
*Texture.*—Flat and smooth, very little rugosity with maturing of the bract.
*Vein color.*—Upper surface: Vein color corresponds closely to the bract color. Lower surface: Vein color pink, from RHS 51 A to 51 B.
*Color.*—Generally a deep medium-red, uniform. Upper surface: RHS 46 B. Lower surface: Between RHS 46 B and 46 C.
*Petiole.*—10–15 mm long; color: upper side deep red, between RHS 46 A and 46 B, lower side pink, near RHS 51 B.
Cyme: 8–10 cyathia borne in a tight cluster, 20–25 mm in diameter.
Cyathium: Ovate, about 6 mm in diameter, medium to light green colored, RHS 143 B to 143 C, top red, RHS 46 B.
Peduncle: Light green, RHS 144 B, about 4–6 mm long.
Nectar cups: Usually only one per cyathium: about 5 mm in diameter, mainly golden yellow, RHS 15 A, partly reddish infused near the margin, approximately RHS 40 A.
Reproductive organs:
*Stamens.*—About 20 per cyathium, red filaments, RHS 46 B, moderate pollen, yellow RHS 12 A.
*Pistil.*—1 per cyathium, style and stigma red, RHS 46 B, stigma trifurcate, 6-lobed.
*Ovary.*—Light to medium green, RHS 143B, triangular, diameter 3–4 mm, 5–6 mm long, 3 ovules.
*Fruit/seed set.*—None observed to date.

I claim:

1. A new and distinct cultivar of Poinsettia plant named 'Fismond', as illustrated and described herein.

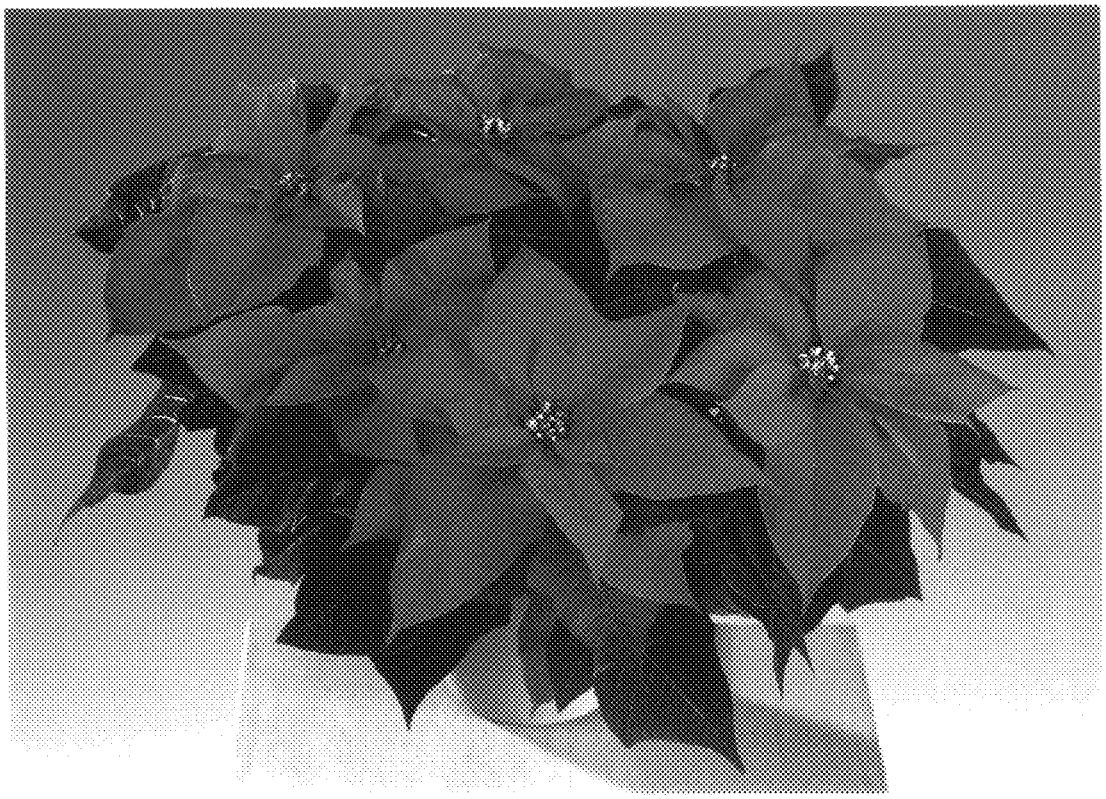

* * * * *